(12) United States Patent
Mehrkesh et al.

(10) Patent No.: US 10,465,950 B2
(45) Date of Patent: Nov. 5, 2019

(54) GUANIDINIUM-BASED IONIC LIQUIDS IN ABSORPTION CHILLERS

(71) Applicant: YAZAKI CORPORATION, Tokyo (JP)

(72) Inventors: Amirhossein Mehrkesh, Camarillo, CA (US); Stefan Maat, Camarillo, CA (US); George G. Tamas, Camarillo, CA (US)

(73) Assignee: YAZAKI CORPORATION, Tokyo (JP)

( * ) Notice: Subject to any disclaimer, the term of this patent is extended or adjusted under 35 U.S.C. 154(b) by 71 days.

(21) Appl. No.: 15/607,240

(22) Filed: May 26, 2017

(65) Prior Publication Data

US 2017/0343251 A1 Nov. 30, 2017

Related U.S. Application Data

(60) Provisional application No. 62/350,993, filed on Jun. 16, 2016, provisional application No. 62/350,968, filed on Jun. 16, 2016, provisional application No. 62/341,736, filed on May 26, 2016.

(51) Int. Cl.

| F25B 15/00 | (2006.01) |
|---|---|
| F25B 15/06 | (2006.01) |
| C07C 277/08 | (2006.01) |
| C07C 279/02 | (2006.01) |

(52) U.S. Cl.
CPC ............ *F25B 15/06* (2013.01); *C07C 277/08* (2013.01); *C07C 279/02* (2013.01); *F25B 15/002* (2013.01); *F25B 2315/001* (2013.01); *Y02A 30/277* (2018.01); *Y02B 30/62* (2013.01)

(58) Field of Classification Search
None
See application file for complete search history.

(56) References Cited

U.S. PATENT DOCUMENTS

| 5,082,968 A | 1/1992 | Brunelle et al. |
|---|---|---|
| 8,506,839 B2 | 8/2013 | Shiflett |
| 2003/0185279 A1 | 10/2003 | Wu et al. |

(Continued)

FOREIGN PATENT DOCUMENTS

| RU | 2502067 C2 | 12/2013 |
|---|---|---|
| WO | 96/01296 A1 | 1/1996 |

(Continued)

OTHER PUBLICATIONS

Notice of Allowance dated Aug. 15, 2018 for U.S. Appl. No. 15/607,079.

(Continued)

*Primary Examiner* — Necholus Ogden, Jr.
(74) *Attorney, Agent, or Firm* — Perkins Coie LLP; Viola T. Kung

(57) ABSTRACT

This invention relates to using a guanidinium-based ionic liquid as an absorbent material in an absorption chiller. The invention provides an absorption chiller comprising a mixture of a refrigerant and an absorbent, and the absorbent is a guanidinium-based ionic liquid. A preferred refrigerant is water. This invention also provides a method for synthesizing N,N,N',N',N'',N''-hexamethylguanidinium acetate.

14 Claims, 3 Drawing Sheets

(56) References Cited

U.S. PATENT DOCUMENTS

| | | |
|---|---|---|
| 2004/0133058 A1 | 7/2004 | Arlt et al. |
| 2007/0144186 A1 | 6/2007 | Shiflett et al. |
| 2008/0028777 A1 | 2/2008 | Boesmann et al. |
| 2010/0132384 A1 | 6/2010 | Shiflett |
| 2010/0326126 A1 | 12/2010 | Seiler et al. |
| 2011/0226004 A1* | 9/2011 | Kontomaris ........... C09K 5/047 62/476 |
| 2011/0247494 A1* | 10/2011 | Dinnage ............ B01D 53/1456 95/92 |
| 2011/0265476 A1 | 11/2011 | Berger et al. |
| 2012/0011886 A1* | 1/2012 | Shiflett .................. C09K 5/047 62/476 |
| 2012/0247144 A1 | 10/2012 | Seiler et al. |
| 2013/0219949 A1 | 8/2013 | Seiler et al. |
| 2013/0327084 A1 | 12/2013 | Shiflett |
| 2015/0007963 A1 | 1/2015 | Kalb |
| 2017/0343251 A1 | 11/2017 | Mehrkesh et al. |

FOREIGN PATENT DOCUMENTS

| | | |
|---|---|---|
| WO | 2008/138832 A1 | 11/2008 |
| WO | 2010/117836 A1 | 10/2010 |
| WO | 2014/082420 A1 | 6/2014 |

OTHER PUBLICATIONS

International Search Report dated Sep. 7, 2017 in International Application No. PCT/US2017/034829.

Prado, et al., "Chanpter 1: Applications of Ionic Liquids", In *Application, Purification, and Recovery of Ionic Liquids, 1st Edition*, Editors: Olga Kuzmina & Jason Hallett, © 2016 Elsevier, Feb. 25, 2016, pp. 1-58.

Non-Final Office Action dated Apr. 6, 2018 in U.S. Appl. No. 15/607,079.

* cited by examiner

GUANIDINIUM-BASED IONIC LIQUIDS IN ABSORPTION CHILLERS

This application claims the benefit of U.S. Provisional Application Nos. 62/341,736, filed May 26, 2016; 62/350,968, filed Jun. 16, 2016; and 62/350,993, filed Jun. 16, 2016. The contents of the above-identified applications are incorporated herein by reference in their entireties.

TECHNICAL FIELD

This invention relates to guanidinium-based ionic liquids, such as hexamethylguanidinium acetate ionic liquid, useful as absorbent materials in absorption chillers. This invention also provides a method for synthesizing N,N,N',N',N'',N''-hexamethylguanidinium acetate.

BACKGROUND

Absorption chillers are designed to generate cooling (chilling) effect by means of generating chilled water which can be used to extract heat from an air flow (e.g. in an air conditioning system). Absorption chillers create a chilling effect by going through a complete absorption-refrigeration cycle. The simultaneous heat and mass transfer of the refrigerant to and from its mixture with the absorbent is the main mechanism of producing the chilling effect in an absorption chiller. The absorbent in the system should have a great tendency towards the refrigerant by dissolving it readily under the operating conditions of the system. The absorption process will make it possible for the system to work at sub-atmospheric pressures (between 0.01-0.1 atm for a water-based absorption chiller) leading to the evaporation of the refrigerant at much lower temperatures than its normal boiling point.

In absorption chillers, the need for an electricity consuming part (i.e. a compressor) to pressurize the refrigerant is addressed through the use of an appropriate absorbent. Latent heat is consumed for the evaporation of the refrigerant, which provides a means of chilling. The low pressure in the evaporator provides the benefit of easy evaporation of the refrigerant (i.e. liquids evaporate easier at lower pressures), thereby making the system capable of producing a chilling effect at low temperatures. However, the very low pressure of the evaporator makes the condensation process of the vapor phase (in order for the cycle to be continued) more challenging. This is where an efficient absorbent is needed to thoroughly absorb the refrigerant vapor (which previously has been cooled by releasing latent heat to a cooling water stream) and to change it back into the liquid phase.

Like any other chemical/physical system, absorption chillers have their own drawbacks and limitations. Certain factors such as the crystallization of the absorbent in the system, or the heat loss from different compartments of the system, can make the system deviate from the ideal performance predicted by thermodynamic-based models. The benefits and drawbacks of conventional absorption chillers are described as follows.

Benefits of an Absorption Chiller:
   Low electricity cost—The only electricity consuming part in the system is a relatively small pump, which is used to circulate the absorbent-refrigerant mixture within the system. This fact makes absorption chillers an ideal choice for countries which do not have well developed infrastructures for the generation of electricity.
   It is a closed system in which almost no refrigerant (commonly water) is wasted.
   Ability to work in both dry and humid climates.

Drawbacks:
   Water-lithium bromide (LiBr) salt is a commonly used refrigerant-absorbent (working) pair in absorption chillers. LiBr is a very efficient absorbent for water refrigerant due to its high hygroscopicity. LiBr, which as a pure salt has a melting temperature of 552° C., can absorb water to a high enough degree such that it becomes completely dissolved in the water it has absorbed. [1]

However, absorption chillers working with LiBr absorbent can only operate within a relatively narrow range of the concentration of LiBr in water. The process is impaired if the solution of LiBr in water is either too concentrated or too dilute. On the one hand, a very low amount of water is insufficient to keep LiBr in the liquid phase due to the high melting point of LiBr (552° C.), causing the absorbent to crystallize out of the liquid working pair [2]. On the other hand, a very high amount of water (too dilute of a solution) will completely cover and solvate the $Li^+$ cations and $Br^-$ anions, disturbing the capability of the system to work continuously and efficiently. A narrow (~5%) change in LiBr concentration in the water (from ~57% LiBr/43% water in the diluted stream to ~62% LiBr/38% water in the concentrated stream) is typically required to produce an acceptable amount of cooling load while preventing the solution from being too concentrated or too dilute.

Another drawback of LiBr salt as an absorbent is its corrosiveness, necessitating the use of costly corrosion inhibitors and copper piping. Due to the corrosive nature of LiBr and the involved control procedures needed to avoid its crystallization within the system, there is a need for absorption chillers having less problematic absorbent materials compared with LiBr.

DETAILED DESCRIPTION OF THE INVENTION

The present invention relates to a mixture of a refrigerant and a guanidinium-based ionic liquid and the use of the mixture in an absorption chiller. The present invention provides an absorption chiller comprising an absorber compartment and a generator compartment, wherein both compartments comprise a guanidinium-based ionic liquid as an absorbent and water as refrigerant. The present invention provides an efficient absorption chiller by substituting the common LiBr absorbent with a non-corrosive, hygroscopic ionic liquid (IL).

Figure 1:
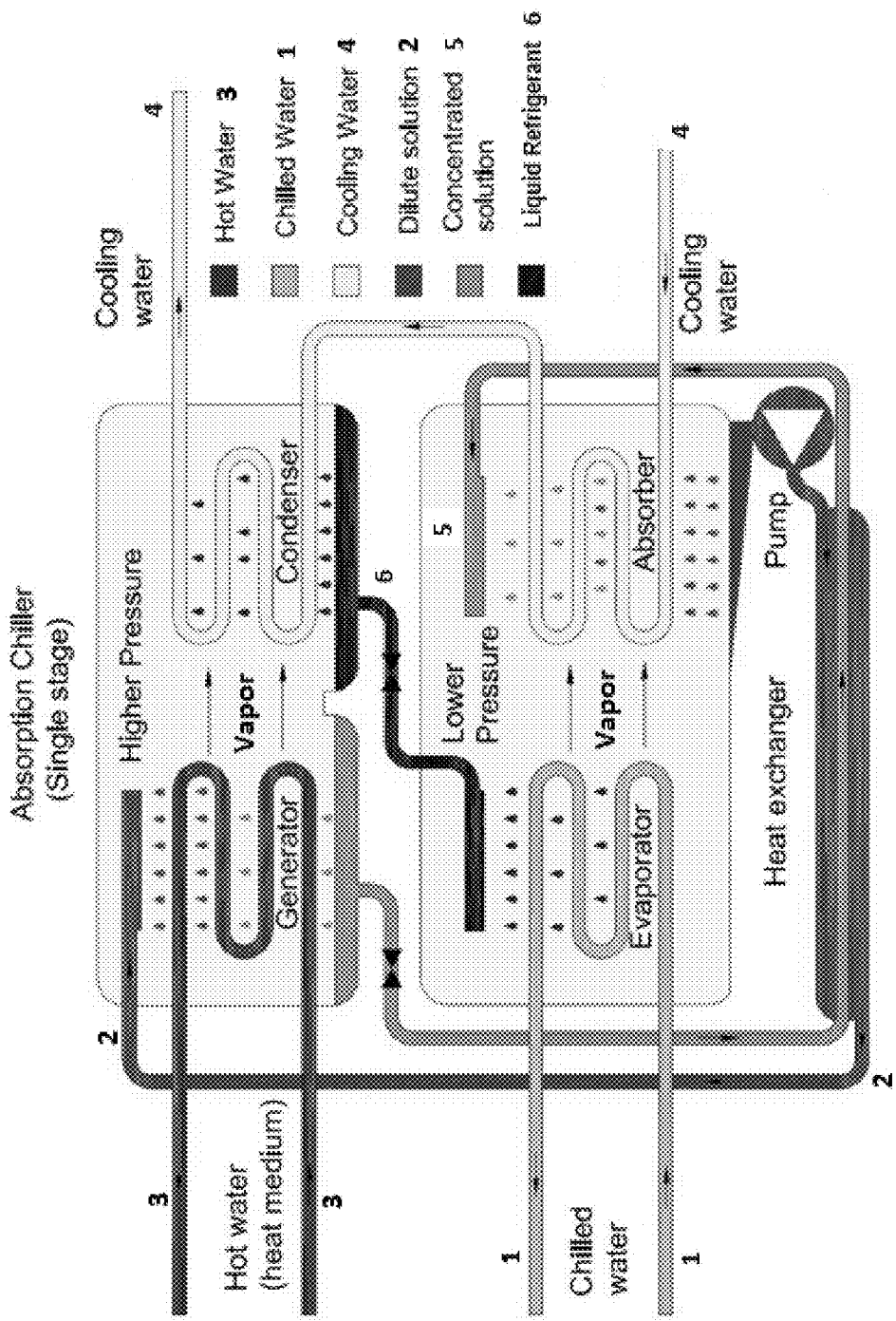
FIG. 1 illustrates an absorption chiller.

FIG. 1 illustrates the schematic of an absorption chiller. An absorption chiller is a machine that utilizes a heat source (e.g., direct flame, hot water, steam, solar energy, waste heat etc.) to drive a cooling process. A mixture of a refrigerant and an absorbent is present in the absorber compartment and the generator compartment of the system.

In the absorption chiller of the present invention, a working pair comprises an absorbent, which is paired (dissolved) with a liquid refrigerant. A refrigerant is a liquid compound used to undergo evaporation in the evaporator compartment of an absorption chiller to produce a chilling effect. A refrigerant in general has appropriate properties for use in such a system, such as low melting point, low-to-medium boiling point, low toxicity, low flammability, low corrosivity, low viscosity, high thermal conductivity, high wettability, and high heat of evaporation. An absorbent has the role of absorbing the refrigerant vapor in the absorber compartment and transferring the refrigerant from a vapor phase to a liquid phase. The generator compartment has the sole role of transferring a portion of the refrigerant from the liquid phase (in solution with the absorbent) to the vapor phase (partial evaporation), thereby performing a vapor-liquid separation procedure. A pure refrigerant is needed for chilling purposes in the evaporator compartment, and therefore, needs to be evaporated from the liquid solution containing the absorbent. The absorbent material generally has a negative role in the generator compartment, since it decreases the vapor pressure of the refrigerant, hindering its evaporation. However, the existence of absorbent in the generator compartment cannot be avoided due to the fact that it is dissolved in the refrigerant stream (working pair solution) incoming from the absorber compartment. An absorption-refrigeration cycle can be accurately modeled using fundamental thermodynamics.

Water is a preferred refrigerant because it is cheap and readily available. Water is non-toxic, non-flammable, and non-explosive, and has a relatively high liquid range. Water also has an exceptionally high enthalpy of vaporization and specific heat capacity. Due to this combination of properties, water is a good heat transfer medium for heat exchange purposes.

However, despite the general suitability of water as a refrigerant in commercial absorption chillers, it is still desirable that the operating pressure and temperature of these systems be reduced, preferably near or at atmospheric conditions. In this case an organic compound possessing aforementioned properties may be used instead. Ethanol is another example of a refrigerant which can be used in the present invention, having higher volatility than water, which may allow system operation closer to atmospheric pressure and temperature.

An ionic liquid (IL) is a multi-atomic salt with organic or inorganic cations and anions, usually defined as having a melting temperature of 100° C. or lower. Many ionic liquids (ILs) are not strongly hydrophilic due to the organic nature of their cations, the larger size of both their cations and anions compared to water molecules, and the limited amount of mass-based solubility of water in ionic liquids due to their relatively large molecular weight. This renders most ILs unsuitable to use as absorbents with water as the refrigerant in an absorption chiller, and the identification of suitable ILs for this purpose is not a simple task.

For example, 1-butyl-3-methylimidazolium bis[(trifluoromethyl)sulfonyl]imide, ([Bmim]$^+$[Tf2N]$^-$), is a well-known ionic liquid with a molecular weight of 419.4 g/mol. The high molar mass of this ionic liquid means that an equimolar solution with water (1:1), in which 1 mole of ionic liquid is dissolved in 1 mole of water, is equivalent to a solution with only 4.11% by mass of water. In this case, the "working pair" of Bmim Tf2N (absorbent) and water (refrigerant) contains an insufficient amount of refrigerant (water) to be of practical use in absorption chillers.

The ionic liquid suitable for the present invention has a high hygroscopic effect comparable to that of LiBr; it has a reasonably low viscosity when diluted with water, and it exhibits desired properties such as non-corrosiveness and a lower risk of crystallization when compared with LiBr. Suitable ionic liquids for the present invention include a non-corrosive ionic liquid with a melting point ($T_m$) lower than 400 K, preferably lower than 350 K, and kinematic viscosity of lower than 25 centistokes, preferably lower than 15 centistokes, when in solution with water.

In absorption chillers, the mass basis concentration of the refrigerant (e.g. water) in the absorbent-refrigerant mixture needs to be reasonably high. This is important to ensure that the working pair can have a suitably low viscosity and that the system can achieve a sufficiently high coefficient of performance (COP). Therefore, suitable ionic liquids for the present invention in general have low molecular weights, preferably lower than 350 g/mol, and more preferably lower than 250 g/mol. Also, it is more preferable to use an ionic liquid absorbent with relatively higher hygroscopic properties (greater affinity for water).

The inventors have discovered that low molecular weight hygroscopic ionic liquids such as guanidinium-based ionic liquids are suitable to be used as absorbent in absorption chillers. In one embodiment of the invention, the guanidinium cation is functionalized with one or more alkyl groups (e.g., one to six methyl, ethyl, propyl, or any combination thereof). Preferably, the guanidinium cation is functionalized with one to six methyl or ethyl groups or a combination thereof, or more preferably, with one to six methyl groups. In one embodiment of the invention, the ionic liquid has a hexamethylguanidinium cation. In another embodiment, the ionic liquid has a hexaethylguanidinium cation. In yet another embodiment, the ionic liquid has an anion with a high tendency toward water such as an acetate anion. A preferred ionic liquid for the present invention is hexamethylguanidinium acetate.

The inventors have discovered that ionic liquids with guanidinium-based cations show a higher potential for water absorption. The melting point and viscosity of pure ionic liquids, such as guanidinium-based ionic liquids, are typically lower than those of pure LiBr salt. Therefore, unlike LiBr-water pair, in order to produce operable ionic liquid-water working pairs including those incorporating guanidinium-based ionic liquids, a mixture of ionic liquid and water with 40% or 50% mass of water (as is the case of for the LiBr-water working pair) in the solution is not required. A solution of ionic liquid with water in which at least 10% (by weight) of water is present in the concentrated solution, and at least 15% (by weight) in the diluted solution, would be sufficient to meet the viscosity and melting point requirements for use in absorption chillers. Guanidinium-based ionic liquid-water working pairs are particularly preferable for use in absorption chillers because (i) guanidinium-based ILs have a high affinity for water compared to common ionic liquids such as 1-butyl-3-methylimidazolium bis[(trifluoromethyl)sulfonyl]imide (Bmim Tf2N), 1-butyl-3-methylimidazolium tetrafluoroborate (Bmim $BF_4$), 1-butyl-3-methylimidazolium hexafluorophosphate (Bmim $PF_6$), or 1-ethyl-3-methylimidazolium tetrafluoroborate (Emim $BF_4$), (ii) the working pair has a sufficiently low viscosity such that the circulation of the absorbent-refrigerant mixture within the system does not create an unreasonable strain on the system components, and (iii) the crystallization temperature of a guanidinium-based IL in a refrigerant is low to avoid the crystallization of the ionic liquid in the system.

The present application also provides a method for synthesizing N,N,N',N',N'',N''-hexamethylguanidinium acetate (6MeGuaOAc). The method comprises the steps of (a) reacting 1,1,3,3,-tetramethylurea with oxalyl chloride to form N-[chloro(dimethylamino)methylene]-N,N-dimethylchloride (4MeUCl); (b) reacting 4MeUCl with N,N-dimethyltrimethylsilylamine to form N,N,N',N',N'',N''-hexamethylguanidinium chloride (6MeGuaCl), and (c) reacting 6MeGuaCl with silver acetate to form 6MeGuaOAc.

In step (a), 1,1,3,3,-tetramethylurea is reacted with oxalyl chloride in a first organic solvent to form N-[chloro(dimethylamino)methylene]-N,N-dimethylchloride (4MeUCl) at room temperature for 12-36 hours (e.g., 24 hours). A first organic solvent includes, but is not limited to toluene, xylene, benzene, or any combination thereof. After the reaction, the excess amount of oxalyl chloride is removed.

In step (b), 4MeUCl is reacted with a molar excess of N,N-dimethyltrimethylsilylamine in a second organic solvent to form N,N,N',N',N'',N''-hexamethylguanidinium chloride (6MeGuaCl) at 20-40 ° C. for 2-6 hours. A second organic solvent includes, but is not limited to tetrahydrofuran, acetonitrile, 1,4-dioxane, or any combination thereof.

In step (c), 6MeGuaCl is reacted with about equimolar amount of silver acetate in a third organic solvent at 40-60° C. for 16-30 hours. A third organic solvent includes, but is not limited to acetonitrile, methanol, acetone, or any combination thereof. After the reaction, silver chloride is separated out as a precipitate, and the final product is dried.

The following examples further illustrate the present invention. These examples are intended merely to be illustrative of the present invention and are not to be construed as being limiting.

EXAMPLES

The thermo-dynamic COP (Coefficient of Performance) of an absorption chiller is defined as the amount of cooling load generated in the evaporator, $Q_E$, (in kilowatt [kW]) divided by the amount of thermal/heat energy, $Q_G$, (in kilowatt [kW]) used to heat up the dilute solution in the generator in order to release refrigerant vapor. A high COP is desirable meaning that for a given expense being paid (thermal energy being used), more work (cooling load) is being delivered. The COP however does not take into account the quality or cost of the thermal/heat energy $Q_G$ used.

The thermodynamic ECOP (Exergetic COP) takes the quality of heat being used into consideration.

$$ECOP = COP \frac{\left(\frac{T_0}{T_E} - 1\right)}{\left(1 - \frac{T_0}{T_h}\right)}$$

Where $T_0=298$ K is the room temperature, $T_E$ the temperature in the evaporator and $T_h=T_G+(5$ to $10$ K$)$ is the heat source temperature, with $T_G$ being the temperature in the generator compartment. [2] Use of waste heat or a thermal stream with a lower temperature (i.e., a lower $T_G$) will eventually increase the ECOP pointing towards a more economical process.

Example 1

Performance Comparison of Guanidinium-based Ionic Liquids and LiBr as Absorbents in an Absorption Chiller In the following example, certain thermo-physical properties of hexaalkylguanidinium-based ILs and LiBr are shown. The guanidinium-based ILs in water are less corrosive working pairs than LiBr in water.

A Continuum Solvation Model (CSM) based on the concept of dielectric constant [3-7] was used to predict the solubility values, the melting point, and the viscosity of hexamethylguanidinium-based ILs and the eutectic mixture of hexamethylguanidinium-based ILs. Ab initio calculations using density functional theory (DFT) were utilized to calculate the molecular structure/geometry along with the electric charge density as an input to the CSM calculations. The results of the computations along with experimental results for LiBr are shown in Table 2.

Table 1 lists the theoretical values of COP and ECOP along with the concentration of absorbent (Mass % Ionic Liquid or LiBr) in both diluted and concentrated mixtures in an absorption chiller with different guanidinium-based ionic salts. As shown in Table 1, in the case of having a large and highly hydrophobic anion such as bis(trifluoromethylsulfonyl)imide (Tf$_2$n), the anion will dominate the process and make the properties of the final ionic liquid less desirable.

TABLE 1

Comparison on the performance of guanidinium-based ionic liquids, and LiBr-water absorption chillers.
Temperatures of evaporator, absorber, and condenser are 5° C., 35° C., and 40° C., respectively.

| Absorbent | COP Predicted | ECOP Predicted | Mass % absorbent (Diluted) | Mass % absorbent (Concentrated) | $T_m$ (K) Predicted | Kinematic Viscosity of Concentrated Solution at 60° C. (cst) Predicted |
|---|---|---|---|---|---|---|
| Hexamethylguanidinium Acetate | 0.768 | 0.314 | 82.2 | 87.2 | 335.3 | 10.84 |
| Hexaethylguanidinium Acetate | 0.769 | 0.304 | 85.9 | 90.9 | 312.75 | 20.88 |
| Hexapropylguanidinium Acetate | 0.766 | 0.289 | 89.2 | 94.2 | 290 | 43.13 |
| Hexamethylguanidinium DMP | 0.782 | 0.305 | 88.97 | 93.97 | 377.8 | 31.80 |
| Hexamethylguanidinium Tf$_2$n | <<0.7 (N/O) | <<0.3 (N/O) | 98 | 98 + 5 (N/O) | — | — |
| LiBr[1] (comparative) | 0.775$^{exp}$ | 0.291$^{exp}$ | 57$^{exp}$ | 62$^{exp}$ | 825$^{exp}$ | 2.04$^{exp}$ |

$^{exp}$Experimental data;
N/O: Not operable

Table 1 shows that hexamethylguanidinium acetate ionic liquid absorbs higher amounts of water compared to other ionic liquids listed (better hygroscopic properties). The hexamethylguanidinium acetate ionic liquid can be diluted up to the point of having ~18% (wt %) of water in the solution. This extra amount of water decreases the viscosity of the final ionic liquid-water mixture.

As also shown in Table 1, hexamethylguanidinium acetate ionic liquid has a predicted melting point of 335.3 K, which is significantly lower than the melting point of LiBr (825 K). A lower melting point of an ionic liquid is desirable because it decreases the risk of crystallization of the absorbent within the system. When hexamethylguanidinium acetate ionic liquid-water mixture is concentrated down to 13% mass of water, a kinematic viscosity of 10.84 cst at 60° C. is achieved. This viscosity value is lower than the viscosity of other concentrated ionic liquid-water pairs listed in Table 1. This is mainly due to the high hygroscopic properties of hexamethylguanidinium acetate ionic liquid, meaning that it can absorb more water (become more diluted) which can help in decreasing the viscosity of the mixture. Lowering the viscosity of the absorbent-refrigerant mixture improves the efficiency of the absorption chillers substantially.

Example 2

Synthesis of Hexamethylguanidinium Acetate

The synthesis of N,N,N',N',N'',N''-hexamethylguanidinium acetate (6MeGuaOAc) was accomplished through a three-step protocol.

Figure 2:
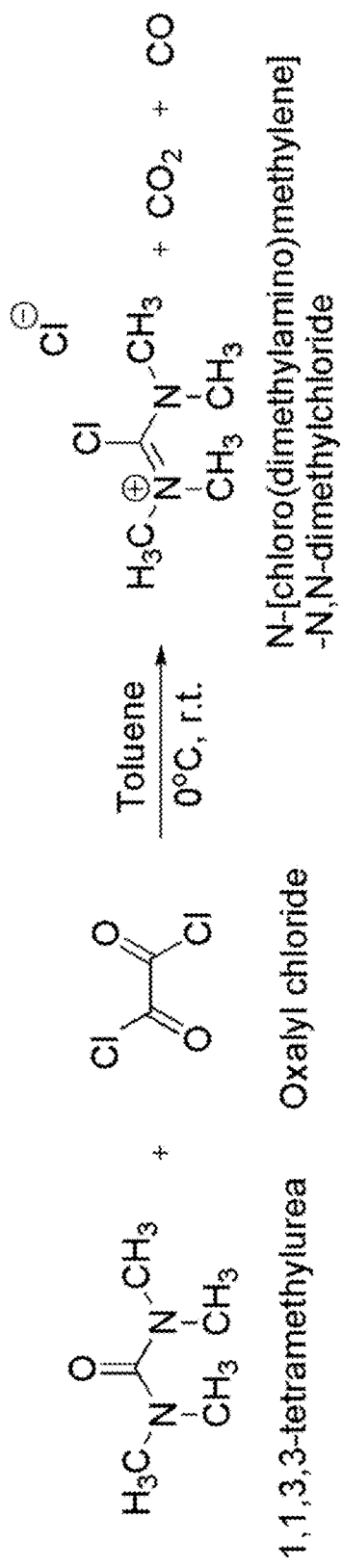
FIG. 2 shows the reaction scheme for synthesis of N-[chloro(dimethylamino)methylene]-N,N-dimethylchloride (4MeUCl) from 1,1,3,3-tetramethylurea (4MeUrea) and oxalyl chloride (OxalylCl).

I. In the first step, 1,1,3,3-tetramethylurea (4MeUrea) was converted to N-[chloro(dimethylamino)methylene]-N,N-dimethylchloride (4MeUCl). This reaction was performed under completely moisture-free conditions by necessity. UHP argon was used to provide an inert atmosphere. As shown in FIG. 2., 1,1,3,3-tetramethylurea , in presence of 1:5 excess amount of oxalyl chloride added dropwise at 0° C., generated 4MeUCl.

6.44 mL of 1,1,3,3-tetramethylurea (99%, d=0.969 g/mL) and 40 mL toluene were added to a three-neck round bottom (3rb) flask and left for 15 minutes under stirring to reach the ice bath temperature.

23.18 mL of oxalyl chloride were slowly added to the three-neck flask with an automated syringe at a rate of 0.01 mL/min. After the addition was finished, the ice-bath was removed and the mixture was left to stir for 24 hours at room temperature.

A slightly yellow solid product was formed. The flask was then taken off the condenser and the solvent (i.e. toluene) and the excess amount of oxalyl chloride were removed in vacuo with the rotary evaporator set at 55° C. and 25 mbar. The intermediate was left under high vacuum to fully dry for 48 hours.

Figure 3:
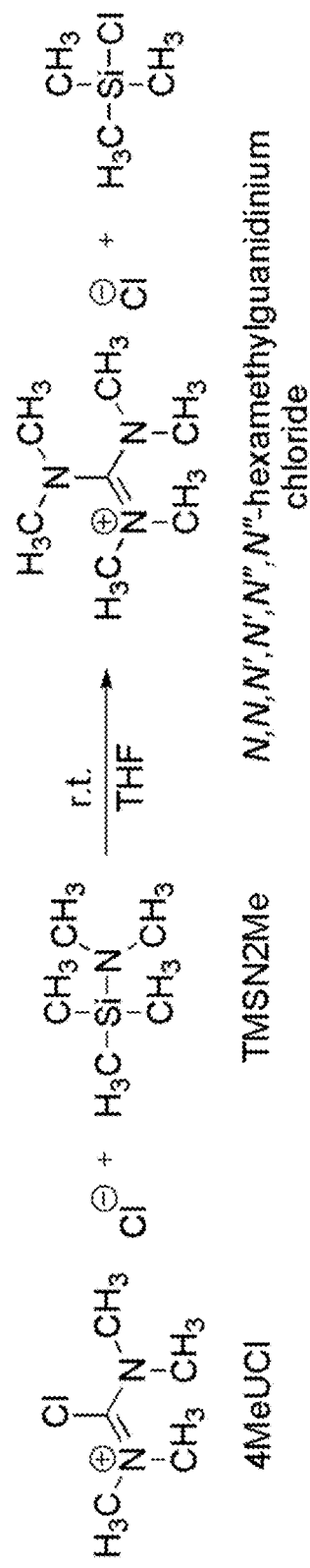
FIG. 3 shows the reaction scheme for synthesis of N,N,N',N',N'',N''-hexamethylguanidinium chloride (6MeGuaCl) from 4MeUCl in presence of 1:2 excess N,N-dimethyltrimethylsilylamine (TMSN2Me), using extra-dry THF as solvent.

II. In the second step, 4MeUCl was converted to N,N,N',N',N'',N''-hexamethylguanidinium chloride (6MeGuaCl) in presence of 1:2 excess N,N-dimethyltrimethylsilylamine (TMSN2Me), using extra-dry THF as solvent, as shown in FIG. 3.

4.81 g of 4MeUCl (99%) and 80 mL tetrahydrofuran (THF) were added to a three-neck round bottom (3rb) flask and left for 15 minutes under stirring to reach the ice bath temperature.

9.30 mL (97%, d=0.723 g/cm3) of N,N-dimethyltrimethylsilylamine (TMSN2Me) were slowly added to the three-neck flask with an automated syringe at a rate of 0.2 mL/min. After the addition was finished, the ice-bath was removed and the mixture was left to stir for 1 hour at room temperature and another 2 hours at 35° C.

The crude product, a light yellow liquid, was then processed in a rotary evaporator at 55° C. and 25 mbar for 1 hour and then kept under high vacuum for another 24 hours to fully remove any trace amount of solvent. The by-product TMS-Cl, with a boiling point of 57° C., was removed during this procedure, a chromatographic purification not being further required.

Figure 4:
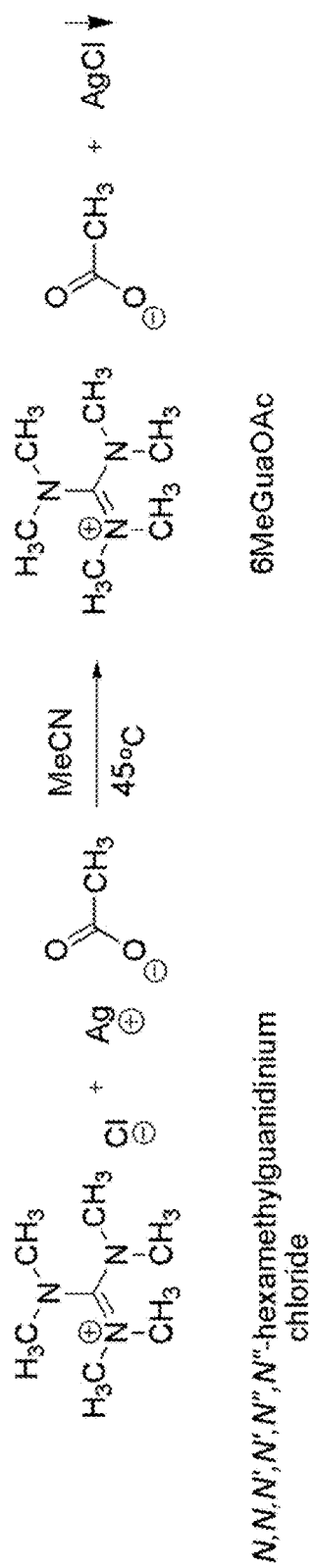
FIG. 4 shows the reaction scheme for synthesis of N,N,N',N',N'',N''-hexamethylguanidinium acetate (6MeGuaOAc) from 6MeGuaCl via a metathesis reaction in presence of equimolar amount of silver acetate.

III. In the third step, 6MeGuaOAc was synthesized from 6MeGuaCl via a metathesis reaction in presence of equimolar amount of silver acetate, as shown in FIG. 4.

9.24 g of 6MeGuaCl (99%) and 8.58 g of AgOAc (99%, photosensitive) were charged to a round bottom (rb) flask. To the rb flask, 150 mL of acetonitrile (ACS grade) were added and then the setup was connected to a Schlenk line and wrapped in aluminum foil. The mixture was left to stir for 24 hours at 45° C. After stirring, the hotplate was turned off and left 15 minutes for phase separation. AgCl separated out as a gray precipitate on the bottom of the rb flask. The slurry was gravitationally filtered through two filter papers. The solvent was removed in vacuo with the rotary evaporator set at 55° C. and 25 mbar. 100 mL of acetone were added to the rb and the flask was stored at low temperature to further allow precipitation of AgCl by-product and then vacuum filtrated. This cycle was repeated multiple times until no AgCl was detected. The final product comprising 6MeGuaOAc was left under high vacuum to fully dry for 48 hours.

The yield of 6MeGuaOAc via this three-step synthesis procedure was 87%, and the purity of the product was 97%.

NMR data for the synthesis product were as follows: $^1$H NMR (500 MHz, DMSO-$d_6$) δ: 2.87 (s, 18H), 1.67 (s, 3H).

It is to be understood that the foregoing describes preferred embodiments of the present invention and that modifications may be made therein without departing from the scope of the present invention as set forth in the claims.

REFERENCES

[1] Zhang, X., & Hu, D. (2011). Performance simulation of the absorption chiller using water and ionic liquid 1-ethyl-3-methylimidazolium dimethylphosphate as the working pair. *Applied Thermal Engineering*, 31(16), 3316-3321.
[2] Al-Tahaineh, H., Frihat, M., and Al-Rashdan, M. (2013). Exergy Analysis of a Single-Effect Water-Lithium Bromide Absorption Chiller Powered by Waste Energy Source for Different Cooling Capacities. *Energy and Power* 3(6), 106-118.
[3] Klamt, A., & Schiffirmann, G. J. G. J. (1993). COSMO: a new approach to dielectric screening in solvents with explicit expressions for the screening energy and its gradient. *Journal of the Chemical Society, Perkin Transactions* 2, (5), 799-805.
[4] Klamt, A. (1995). Conductor-like screening model for real solvents: a new approach to the quantitative calculation of solvation phenomena. *The Journal of Physical Chemistry*, 99(7), 2224-2235.
[5] Eckert, F., & Klamt, A. (2002). Fast solvent screening via quantum chemistry: COSMO-RS approach. *AIChE Journal*, 48(2), 369-385.
[6] Tomasi, J., Mennucci, B., & Cammi, R. (2005). Quantum mechanical continuum solvation models. *Chemical reviews*, 105(8), 2999-3094.

[7] Klamt, A., Eckert, F., Hornig, M., Beck, M. E., & Burger, T. (2002). Prediction of aqueous solubility of drugs and pesticides with COSMO-RS. *Journal of computational chemistry*, 23(2), 275-281.

What is claimed is:

1. An absorption chiller comprising an absorber compartment and a generator compartment, wherein both compartments comprise a mixture of a refrigerant and an absorbent, and the absorbent is a guanidinium-based ionic liquid, wherein the ionic liquid has an acetate anion.

2. The absorption chiller of claim 1, wherein the refrigerant is water.

3. The absorption chiller of claim 1, wherein the ionic liquid has a melting point of 400K or less.

4. The absorption chiller of claim 1, wherein the ionic liquid has a kinematic viscosity lower than 25 centistokes.

5. An absorption chiller comprising an absorber compartment and a generator compartment, wherein both compartments comprise a mixture of a refrigerant and an absorbent, and the absorbent is a guanidinium-based ionic liquid, wherein the ionic liquid has a hexamethylguanidinium cation.

6. The absorption chiller of claim 5, wherein the ionic liquid is hexamethylguanidinium acetate.

7. An absorption chiller comprising an absorber compartment and a generator compartment, wherein both compartments comprise a mixture of a refrigerant and an absorbent, and the absorbent is a guanidinium-based ionic liquid, wherein the ionic liquid has a hexaethylguanidinium cation.

8. The absorption chiller of claim 7, wherein the ionic liquid is hexaethylguanidinium acetate.

9. The absorption chiller of claim 5, wherein the refrigerant is water.

10. The absorption chiller of claim 5, wherein the ionic liquid has a melting point of 400K or less.

11. The absorption chiller of claim 5, wherein the ionic liquid has a kinematic viscosity lower than 25 centistokes.

12. The absorption chiller of claim 7, wherein the refrigerant is water.

13. The absorption chiller of claim 7, wherein the ionic liquid has a melting point of 400K or less.

14. The absorption chiller of claim 7, wherein the ionic liquid has a kinematic viscosity lower than 25 centistokes.

* * * * *